United States Patent
Juillerat et al.

(10) Patent No.: US 10,520,483 B2
(45) Date of Patent: Dec. 31, 2019

(54) AUTONOMOUS DEVICE FOR DETECTING CHARACTERISTICS OF A MEDIUM TO BE MEASURED AND METHOD THEREFOR

(71) Applicant: HAMILTON Bonaduz AG, Bonaduz (CH)

(72) Inventors: Frederic Juillerat, Paspels (CH); Yoann Gasteuil, Lyons (FR)

(73) Assignee: Hamilton Bonaduz AG (CH)

( * ) Notice: Subject to any disclaimer, the term of this patent is extended or adjusted under 35 U.S.C. 154(b) by 173 days.

(21) Appl. No.: 15/647,441

(22) Filed: Jul. 12, 2017

(65) Prior Publication Data

US 2018/0053547 A1 Feb. 22, 2018

(30) Foreign Application Priority Data

Aug. 19, 2016 (DE) .................. 10 2016 115 403

(51) Int. Cl.
*G01N 33/18* (2006.01)
*G11C 11/412* (2006.01)
*A61L 2/00* (2006.01)
*B65B 55/16* (2006.01)

(52) U.S. Cl.
CPC ...... *G01N 33/1886* (2013.01); *G11C 11/4125* (2013.01); *A61L 2/0035* (2013.01); *B65B 55/16* (2013.01)

(58) Field of Classification Search
CPC .............. G11C 11/005; G01N 33/1886; G01N 33/48785; C12M 41/48; A61L 2/28; A61L 2/081; A61L 2/0035; A61L 2202/14; B65B 55/16
See application file for complete search history.

(56) References Cited

U.S. PATENT DOCUMENTS

| | | | |
|---|---|---|---|
| 5,022,027 A * | 6/1991 | Rosario | G06F 11/1415 376/245 |
| 6,057,773 A | 5/2000 | Shukla et al. | |
| 2003/0227394 A1* | 12/2003 | Rothgeb | A47L 15/4297 340/870.01 |
| 2009/0289792 A1 | 11/2009 | Potyrailo et al. | |
| 2011/0012736 A1 | 1/2011 | Potyrailo et al. | |
| 2012/0132882 A1* | 5/2012 | Seo | H01L 27/12 257/4 |
| 2014/0062669 A1* | 3/2014 | Mena | G06F 17/40 340/10.5 |
| 2015/0137992 A1* | 5/2015 | Potyrailo | G01N 27/3272 340/870.07 |
| 2015/0306267 A1 | 10/2015 | Selker et al. | |

FOREIGN PATENT DOCUMENTS

WO 2009120231 A1 10/2009

* cited by examiner

*Primary Examiner* — Nathaniel J Kolb
(74) *Attorney, Agent, or Firm* — Jansson Munger McKinley & Kirby Ltd.

(57) ABSTRACT

An autonomous device for detecting characteristics of a medium to be measured is disclosed. The device includes a sensor, a first microcontroller and a second microcontroller. The first microcontroller has a memory which is not resistant against gamma radiation during the sterilization of the device and the second microcontroller has a memory which is resistant against gamma radiation during the sterilization of the device.

14 Claims, 1 Drawing Sheet

AUTONOMOUS DEVICE FOR DETECTING CHARACTERISTICS OF A MEDIUM TO BE MEASURED AND METHOD THEREFOR

CROSS REFERENCE TO RELATED APPLICATION

This application claims priority based on German patent application DE 10 2016 115 403.2 filed Aug. 19, 2016. The entire disclosure and contents of this application is incorporated by reference into the present application.

FIELD OF THE INVENTION

The field is generally related to an autonomous device for detecting characteristics of a medium to be measured and a method therefor and, more particularly, to a sensor unit for measuring characteristics of a medium, which unit is used in many processes in the biopharmaceutical, pharmaceutical, bioengineering, and chemical industries.

BACKGROUND OF THE INVENTION

In processes of this type, sensors are used which can measure many different process parameters and characteristics at any desired time of the process. These sensors are used only a single time, like the disposable or single-use articles such as containers and pipettes, which are being used more and more frequently to increase the output of such processes, to improve the reliability of production, and to minimize production costs and times. Like single-use articles, they must be free of microorganisms during use, i.e., they must be sterile. A standard method of sterilization is so-called "gamma sterilizing", i.e., sterilization by means of radioactive gamma radiation.

Gamma radiation involves electromagnetic rays (gamma rays) which are emitted by radionuclides such as cobalt 60 isotopes (60 Co or $^{60}$Co) and cesium 137 isotopes (137 Cs or $^{137}$Cs). Gamma rays are not decelerated by most materials and can pass through most of the single-use articles used in bioprocesses. Microorganisms such as bacteria, algae, fungi, viruses, etc., are killed by the ionizing radiation as a result of damage to their nucleic acids. Gamma rays, furthermore, are not absorbed by the material and leave no radioactivity behind. Gamma sterilization of single-use articles can be easily controlled in a defined radiation environment and offers the advantage that neither heat, moisture, pressure, nor vacuum acts on the objects to be sterilized. Thus it represents a nonvarying and predictable sterilization method and is advantageous with respect to safety, time, and costs.

A sensor device for detecting physical or chemical characteristics of a liquid is known from, for example US 2003/0227394 A1 and U.S. Pat. No. 6,057,773. The known sensor device comprises a housing, inside of which are a sensor element, a data collection element with a memory and a microcontroller connected to the sensor element for data transmission, a data-exchange device for wireless transmission of the data detected by the sensor element to an external unit, and a power supply unit. The disadvantage of this known sensor device is that it does not offer complex sensor functions, and in addition it comprises components which are not resistant to gamma radiation and is therefore not adapted to the above-described use in biopharmaceutical processes, among others.

It is known from the technology of send-and-receive systems for the automatic and contactless identification and localization of objects and life forms by means of radio waves (RFID) that RFID transponders resistant to gamma rays can be used. An example of an RFID transponder of this type is disclosed in US 2009/0289792 A1. WO 2009/120231 A1 describes a device for the authentication of single-use articles in biopharmaceutical production, which device comprises a gamma radiation-resistant, nonvolatile FRAM memory (Ferroelectric Random Access Memory) on an RFID transponder, wherein the data stored in the FRAM memory remain intact even after the RFID transponder has been sterilized by gamma radiation.

OBJECTS OF THE INVENTION

It is therefore the object of the present invention to provide an autonomous device for detecting characteristics of a medium to be measured, which device can be used without functional limitations even during or after a gamma sterilization process in a wide variety of bioengineering, pharmaceutical, or chemical processes, and which can be produced at low cost, comprises a simple structure, operates at low power consumption, and offers a comprehensive measurement functionality. Another object of the present invention is to provide a method for operating said device.

This object is achieved by the subject matter having the features of claim 1. Advantageous embodiments and configurations are described in the dependent claims.

SUMMARY OF THE INVENTION

According to the invention, an autonomous device for detecting characteristics of a medium to be measured comprises a sensor, a first microcontroller, and a second microcontroller, wherein the first microcontroller comprises a memory which is not resistant to gamma radiation, preferably during the sterilization of the device, and wherein the second microcontroller comprises a memory which is resistant to gamma radiation, preferably during the sterilization of the device. Providing two separate microcontrollers enables the autonomous device to be equipped with multiple functionalities. As a result of the resistance of the memory to gamma radiation, it is ensured that, during the gamma sterilization of the autonomous device, the data stored in the second microcontroller will not be lost. In particular, it is thus possible for the second microcontroller to install the appropriate firmware in the first microcontroller after the gamma sterilization, which firmware may comprise program components adapted to special functions, and thus the autonomous device can be used reliably in biopharmaceutical processes in which gamma sterilization is used. It is thus possible to select low-cost components for the first microcontroller, for example, so that, overall, a considerable cost savings is obtained without the need to sacrifice certain functionalities.

The memory of the second microcontroller is preferably a FRAM (Ferroelectric Random Access Memory) component or possibly even a RRAM (Resistive Random Access Memory) component. Both types of memory components or memory chips are nonvolatile, consume little energy, and are more reliable and faster than EEPROMs. In addition to the FRAM and RRAM or ReRAM memory components cited here, it is also possible to use other memory components known to the expert which are resistant to gamma radiation such as GMRAM (Giant Magneto-Resistance Random Access Memory) or the like.

It is also advantageous for the first microcontroller to be provided with a wireless communications device. The wireless communications device serves to transmit the data acquired by the sensor to an external device preferably in real time, i.e., as soon as the data are detected, so that the characteristics of the medium to be measured can be evaluated and possibly displayed directly, as it were, and immediately by, for example, an external, higher-level device. The wireless communications device can be integrated as a logical function block into the first microcontroller or connected to the first microcontroller by a hardware circuit. A preferred type of wireless communication is Bluetooth technology, but it is also possible to use other suitable wireless communication protocols and interfaces in the first microcontroller.

It is especially preferable for the device to comprise a switching device, which is configured to trigger a switching pulse on contact with the medium to be measured. A switching device of this type advantageously comprises two electrodes, configured so that the electrodes trigger the switching pulse on contact with the medium to be measured. In particular, a switching device can be imagined which triggers the switching pulse when the autonomous device is placed in a liquid medium to be measured. The switching pulse can, for example, turn on or activate the second microcontroller, so that a programmed sequence of steps can be started in the second microcontroller. Alternatively, it is also possible that the switching device could turn on the first microcontroller. In addition to the switching device cited above with two (metal) electrodes, it is also possible to use other switching devices suitably adapted to the same purpose.

It is also preferred that the sensor be configured as a logical function block of the first microcontroller or of the second microcontroller. Modern microcontrollers usually comprise a processor and also peripheral functions at the same time, some of which can perform complex functions such as those of USB or Ethernet interfaces, PWM outputs, LCD controllers, or A/D converters. Microcontrollers can also have programmable digital and/or analog or hybrid function blocks.

The term "function block" should be understood in the context of the present invention as a logical function which is responsible for a specific sequence of steps. A function block can therefore be part of a microcontroller or comprise its own, possibly programmable, circuit or interface components. The first or the second microcontroller comprises a function block which is responsible for the functionality of the sensor. As mentioned above, by means of appropriate programming, i.e., by the installation of firmware, the microcontroller can be provided with the functionality for the sensor after its memory has been erased. Because not necessarily all of the data on a memory component not resistant to gamma radiation become unusable after sterilization, the installation of the firmware ensures that the data of the memory component are overwritten in such a way that the full functionality of the microcontroller, including all of its function blocks, is available.

It is advantageous for the medium to be measured to be a gas, a liquid, or a granulate. In most biopharmaceutical processes, the autonomous devices according to the present invention will be used in liquids.

It is especially advantageous for the function of the sensor to comprise the detection of physical and chemical characteristics of the medium to be measured such as pH value, temperature, viscosity, density, enzyme activity, ion content, conductivity, substance concentration such as oxygen saturation, hardness, pressure, biological activity, radioactivity, flow rate, and the like. The sensor can detect essentially any physical or chemical characteristic of the medium, as long as the technology is available for it and is available within the scope of a programmable function block of a microcontroller. The sensor functionality can be programmed to measure the characteristics of the medium essentially continuously or periodically, i.e., at certain intervals. It is also conceivable that more than one sensor functionality can be provided, i.e., more than one characteristic of the medium can be detected by a single autonomous device.

According to the invention, a method for operating a device for detecting characteristics of a medium to be measured is also provided, this method consisting of the following steps: providing a device as described above; performing a gamma sterilization of the device; activating the second microcontroller by way of an external signal, the second microcontroller then activating the first microcontroller by transferring and starting suitable firmware from the memory of the second microcontroller to the memory of the first microcontroller; and switching on the sensor to enable the detection of the characteristics of the medium to be measured.

This method makes optimal use of the properties of the above-described autonomous device: After a gamma sterilization of the entire autonomous device, the first microcontroller is no longer functional, for the data in its memory have been at least partially damaged or erased by the exposure to gamma rays. When the second microcontroller is turned on by an external signal, e.g., by introducing the autonomous device into a liquid, as a result of which a switching signal is transmitted to the second microcontroller, the firmware is copied from the memory of the second microcontroller to the memory of the first microcontroller, so that the full functionality of the first microcontroller is again available. The memory of the first microcontroller can be empty, or it can also contain data. The firmware also contains the programming of the corresponding function blocks. After that, the sensor or the function block of the corresponding microcontroller is activated, so that the autonomous device can store and process the detected characteristics of the medium and possibly transmit them to an external device.

The second microcontroller is preferably activated by a switching device which triggers a switching pulse on contact with the medium to be measured, as already described above.

After activation of the sensor, it is also advantageous for the first or the second microcontroller to be turned off. Depending on which microcontroller is responsible for the primary functions of detection and transmission and/or storage of the data, the other microcontroller, which, after activation, is no longer fulfilling any function which must remain permanently available, can be turned off for good or for only a certain period of time. Thus the autonomous device can operate in an energy-efficient manner, wherein the service life of the components is also prolonged.

Also according to the invention is a system with a container, preferably a cell culture container, with at least one autonomous device as described above. Systems of this type are needed in biopharmaceutical laboratories for the processes which are conducted there. They comprise in general a cell culture container with the medium to be measured and a plurality of autonomous sensor devices for use in a biopharmaceutical, bioengineering, pharmaceutical, or chemical process.

The system advantageously comprises an analysis and/or display device, so that the values detected during the process can be evaluated, processed, and displayed immediately.

Thus the process parameters can be detected and displayed directly and possibly used as control quantities for certain steps of the process.

The container is preferably configured as a single-use or disposable article. These types of containers for holding the medium must be cleaned of microorganisms or sterilized before every use and are thus subject to the same requirements as the autonomous device according to the present invention.

BRIEF DESCRIPTION OF THE DRAWINGS

The drawings illustrate a preferred embodiment including the above-noted characteristics and features of the device. The device will be readily understood from the descriptions and drawings. In the drawings.

DETAILED DESCRIPTION OF THE EMBODIMENTS

Figure 1:
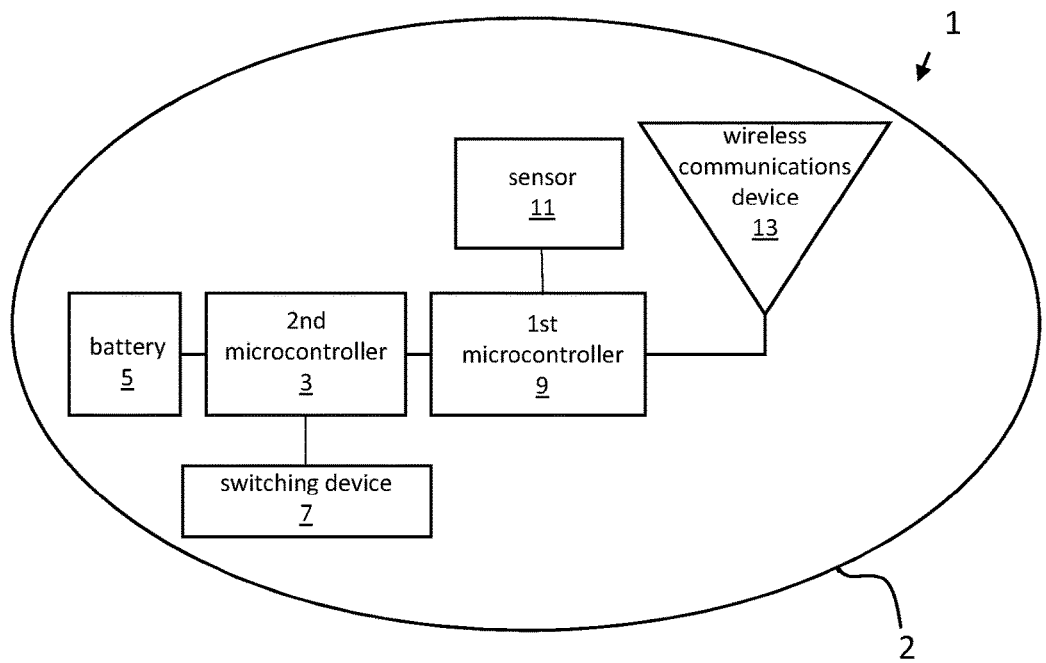
FIG. 1 illustrates a schematic diagram of a first embodiment of the autonomous device of the present invention.

FIG. 1 illustrates a schematic diagram of a first preferred embodiment of the autonomous device according to the present invention, wherein the autonomous device is configured as a sensor ball 1. Sensor ball 1 comprises a waterproof housing 2, the shape of which does not necessarily have to be exactly that of a ball. It could have the shape of an ellipsoid, a cube, a rectangular block, a cylinder, or any other desired, even irregular, combination of these shapes. A plastic material, for example, which is adapted to the processes in question and which is shaped by injection-molding can be considered as housing material. The interior of housing 2 comprises a number of components, including a first microcontroller 9, a second microcontroller 3, a power supply unit or battery 5, a switching device 7, a sensor 11, and a wireless communications device 13.

The central element of autonomous device 1 is second microcontroller 3, which is connected to power supply device 5, to switching device 7, and to first microcontroller 9; second microcontroller 3 comprises a memory component of the FRAM type (Ferroelectric Random Access Memory), which is resistant to gamma radiation during the sterilization of the autonomous device.

Microcontrollers with FRAM memories are obtainable from, for example, Texas Instruments or Fujitsu and are also very frugal in terms of power consumption, highly reliable over a wide temperature range, and, thanks to the FRAM memory technology, considerably faster than microcontrollers with, for example, FLASH memory components. It is also possible to use some other type of gamma radiation-resistant memory for the second microcontroller such as RRAM or ReRAM (Resistive Random Access Memory).

Power supply device 5 can be a battery adapted to these types of electrical circuits or possibly a rechargeable battery. Switching device 7 in the preferred embodiment is configured in such a way that it comprises two electrodes (not shown in the figures), which extend to the surface of housing 2 of autonomous device 1, so that, as soon as the two electrodes come in contact with the liquid, a switching pulse is triggered, which is transmitted to second microcontroller 3. Switching device 7 is also supplied with energy by power supply device 5, wherein the lines run by way of second microcontroller 3. Switching device 7 is designed in particular for low power consumption; its function will be described further below with reference to the overall functionality of autonomous device 1.

First microcontroller 9 is connected to second microcontroller 3 and, in contrast to it, comprises a memory component which is not resistant to gamma radiation during the sterilization of sensor ball 1. For this reason, a low-cost, standard commercial memory component can be used in the first microcontroller, e.g., an EPROM or flash memory component. First microcontroller 9 is also supplied by power supply device 5, wherein, in this case as well, the power is supplied by way of second microcontroller 3. First microcontroller 9 comprises an interface to sensor 11 and a corresponding logical function block, which is responsible for processing the signals detected by sensor 11. It is possible for first microcontroller 9 to comprise more than one sensor 11, so that more than one characteristic of a medium can be detected and transmitted by a single sensor ball.

First microcontroller 9, furthermore, is connected to a wireless communications device 13, which, in the preferred embodiment, is configured as a Bluetooth module, preferably on the chip of first microcontroller 9. In addition to Bluetooth, other wireless data transmission technologies adapted to the purpose can also be used such as those of the IEEE 802.11 family or the like. Wireless communications device 13 handles the data traffic between first microcontroller 9 and an external transmitter/receiver, so that, for example, the process parameters detected by sensor 11 can be transmitted in real time, as it were, from first microcontroller 9 to the outside and then evaluated and processed.

In the following, the way in which the preferred embodiment of the autonomous device according to the invention described above functions and thus also the method according to the invention for operating a device for detecting characteristics of a medium to be measured are described. In the turned-off state, i.e., immediately before use in, for example, a biopharmaceutical process, the autonomous device, i.e., sensor ball 1 according to the preferred embodiment, is in the state in which first microcontroller 9 is turned off, i.e., is not functional.

Second microcontroller 3 is in sleep mode or on standby while it is waiting for an external stimulus which will put it in the active state, and switching device 7 is also in sleep mode or on standby, so that it is ready to detect when the corresponding physical conditions for the transmission of a switching pulse are present. Like first microcontroller 9, the two peripheral functions of first microcontroller 9, i.e., sensor 11 and wireless communications device 13, are not turned on or not functional and therefore do not consume any power. This is the situation before and after the gamma sterilization of the autonomous device, for the gamma radiation does not change the state of second microcontroller 3, of battery 5, or of switching device 7, because the FRAM memory component of second microcontroller 3 is resistant to gamma radiation, as is switching device 7 also.

In contrast, the memory component of first microcontroller 9 is empty or loses at least some of its stored data when exposed to gamma radiation. Accordingly, the interfaces to sensor 11 and to wireless communications device 13 are nonfunctioning. The situation described here is therefore the state existing before and after the cleaning or sterilization process and thus also the state in which sensor ball 1 is stored.

The next step in the use according to the invention of the autonomous device or sensor ball 1 is the activation from the storage state. In the preferred embodiment shown here, sensor ball 1 is immersed into a liquid, i.e., the medium to be measured, as a result of which switching device 7 triggers a switching pulse by means of the two electrodes present at the surface of housing 2 and transmits this switching pulse to second microcontroller 3. Second microcontroller 3 thus receives the activation signal for its intended function, leaves sleep mode or standby mode, and turns on first microcontroller 9, thus activating it; this is done in that, first, appropriate firmware containing appropriate programming commands is copied from the FRAM memory component of second microcontroller 3 to the memory component of first microcontroller 9 and installed there.

Next, the corresponding programming commands are installed in the same way by the firmware in the function blocks responsible for the interface connections of sensor 11 and of wireless communications device 13 to first microcontroller 9. After the firmware has been completely installed, including the function block programming, a process which usually takes several seconds, all of the necessary functions of sensor ball 1 are available: the measurements of sensor 11 are carried out, and the results of the measurement are possibly transmitted by first microcontroller 9 via wireless communications device 13 to the outside. Simultaneously, second microcontroller 3 can be put into sleep mode or on standby again, because its functionality is not needed for the detection of the desired data or for the communication of the data to the outside. Thus, resources are conserved, in particular with respect to the power supplied by power supply device 5.

Sensor ball 1 remains in this active state until power supply device 5 can no longer supply any power or another sterilization of autonomous device 1 by exposure to gamma radiation occurs. The gamma sterilization damage or erases the memory component of first microcontroller 9, which is not resistant to such radiation and thus also erases all of the functional programming of the interfaces to sensor 11 and to wireless communications device 13. It is therefore, no longer possible for data to be acquired or for this data to be transmitted. Sensor ball 1 is thus again in its storage state, which has already been described above. The application cycle can thus begin again from the beginning.

Figure 2:
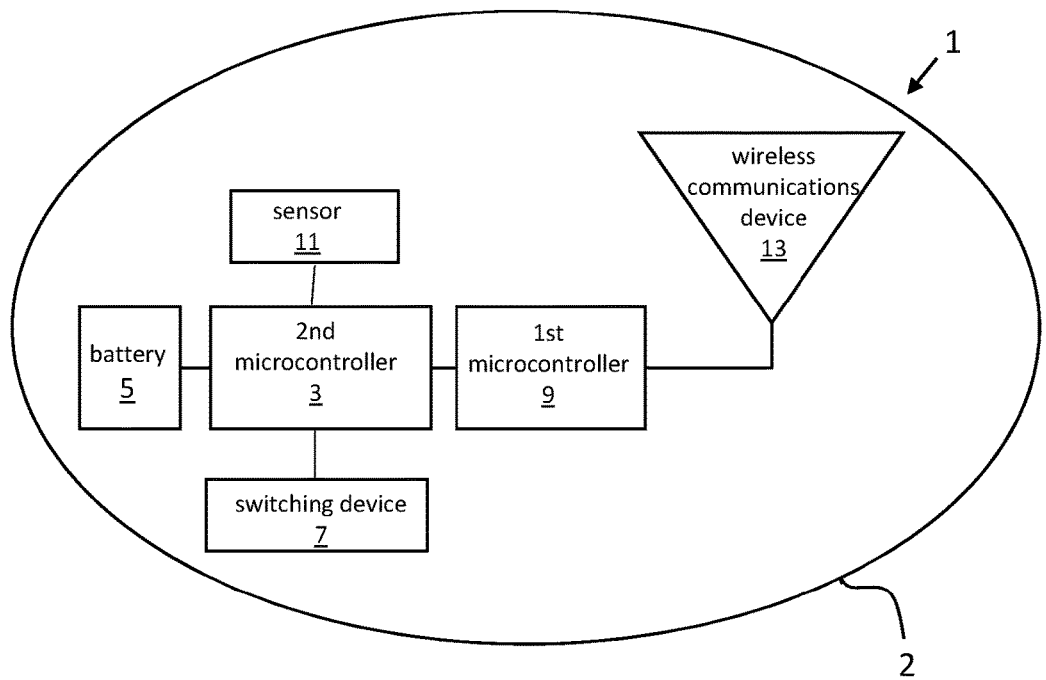
FIG. 2 illustrates a schematic diagram of a second embodiment of the autonomous device of the present invention.

FIG. 2 shows a schematic diagram of a second embodiment of the autonomous device according to the present invention. Because the components used here are essentially the same as those already discussed with respect to FIG. 1, they will not be described again here; only the differences between the first and second embodiments will be pointed out.

In contrast to the first embodiment, sensor 11 in the second embodiment is not connected to first microcontroller 9 but rather to second microcontroller 3. The functional processing, including the digitization, of the data detected by sensor 11 thus takes place in second microcontroller 3.

With respect to the function or to the method for the use of the autonomous device, the result is that, after the firmware has been installed in first microcontroller 9, second microcontroller 3 in the second embodiment may not be put into sleep mode or on standby, because it must remain active so that it can process the signals acquired by sensor 11. The digital processing therefore occurs in second microcontroller 3, and the corresponding data are then transmitted to first microcontroller 9 and from there via wireless communications device 13 to the external data processing system.

Another difference from the first embodiment is that the memory component of second microcontroller 3 is a RRAM (Resistive Random Access Memory) component, which is also resistant to the influences of gamma radiation during the gamma sterilization of sensor ball 1.

An advantage of the second embodiment over the first embodiment is that first microcontroller 9 has fewer functions and therefore can have smaller dimensions and thus be lower in cost. Against this is the fact that second microcontroller 3 must remain turned on and active during the entire active measuring state of autonomous device 1.

It is conceivable according to the invention that an autonomous device could comprise a combination of the two embodiments outlined above; for example, both the first and the second microcontroller could each have its own sensor functionality.

The subject matter of the present invention provides an autonomous device for detecting characteristics of a medium to be measured, which can be used without functional limitations even during or after gamma sterilization in a wide variety of bioengineering, pharmaceutical, or chemical processes, and which can be produced at low cost, has a simple structure, operates on low power, and comprises comprehensive measurement functionality.

A wide variety of materials are available for the various parts discussed and illustrated herein. While the principles of this device have been described in connection with specific embodiments, it should be understood clearly that these descriptions are made only by way of example and are not intended to limit the scope of the device.

The invention claimed is:

1. A sensor unit for detecting characteristics of a medium to be measured having a housing with an interior, the interior of the housing comprising a sensor, a first microcontroller and a second microcontroller, wherein the first microcontroller includes a memory which is not resistant against gamma radiation during a sterilization of the sensor unit and the second microcontroller has a memory which is resistant against gamma radiation during sterilization of the sensor unit.

2. The sensor unit according to claim 1 wherein the memory of the second microcontroller is a FRAM (Ferroelectric Random Access Memory) component.

3. The sensor unit according to claim 1 wherein the memory of the second microcontroller is a RRAM (Resistive Random Access Memory) component.

4. The sensor unit according to claim 1 wherein the sensor unit is configured as a sensor ball and the first microcontroller is provided with a wireless communications device.

5. The sensor unit according to claim 1 further comprising a switching device configured to trigger a switching pulse on contact with the medium to be measured.

6. The sensor unit according to claim 5 wherein the switching device comprises two electrodes configured to trigger the switching pulse on contact with the medium to be measured.

7. The sensor unit according to claim 1 wherein the medium to be measured is a gas, a liquid or a granulate.

8. The sensor unit according to claim 1 wherein the function of the sensor comprises detecting at least one of physical or chemical characteristics of the medium to be measured said characteristics comprising at least one of: pH value, temperature, viscosity, density, enzyme activity, ion content, conductivity, substance concentration, hardness, pressure, biological activity, radioactivity and flow rate.

9. A system having a cell culture container, the system comprising at least one sensor unit according to claim 1.

10. The system of claim 9 further including an analysis or display device.

11. The system of claim 9 wherein the container is configured as a single-use or disposable article.

12. A method for operating a sensor unit for detecting the characteristics of a medium comprising:
   providing a sensor unit having a housing with an interior, the interior comprising a sensor, a first microcontroller and a second microcontroller, wherein the first microcontroller comprises a memory which is not resistant against gamma radiation during a sterilization of the sensor unit, and the second microcontroller comprises a memory which is resistant against gamma radiation during sterilization of the sensor unit;
   performing a gamma sterilization of the sensor unit;
   activating the second microcontroller by way of an external signal, the second microcontroller then activating the first microcontroller by transferring and starting suitable firmware from the memory of the second microcontroller to the memory of the first microcontroller, and
   switching on the sensor to enable the detection of the characteristics of the medium to be measured.

13. The method of claim 12 wherein the second microcontroller is activated by a switching device which triggers a switching pulse on contact with the medium to be measured.

14. The method of claim 12 wherein after activation of the sensor the first or second microcontroller is turned off.

* * * * *